United States Patent [19]

Samaan et al.

[11] Patent Number: 5,684,158

[45] Date of Patent: Nov. 4, 1997

[54] [3-AMINO]-TETRAHYDROCARBAZOLE-PROPANOIC ACID ESTERS

[75] Inventors: Samir Samaan; Joachim Lanz; Paul Naab; Ulrich Rosentreter, all of Wuppertal, Germany

[73] Assignee: Bayer Aktiengesellschaft, Leverkusen, Germany

[21] Appl. No.: 605,412

[22] Filed: Feb. 22, 1996

[30] Foreign Application Priority Data

Feb. 27, 1995 [DE] Germany .................. 195 06 739.8

[51] Int. Cl.$^6$ .................................. C07D 209/88
[52] U.S. Cl. .................................. 548/449; 548/439
[58] Field of Search .................................. 548/449

[56] References Cited

U.S. PATENT DOCUMENTS 4,988,820  1/1991  Boshagen et al. .

FOREIGN PATENT DOCUMENTS 0138491  4/1985  European Pat. Off. .
0425906  5/1991  European Pat. Off. .
0451634  10/1991 European Pat. Off. .
2652447  6/1977  Germany .

OTHER PUBLICATIONS

Chemical Abstracts, vol. 102, abstract No. 1325616, p.6 (1985).

Chemical Abstracts, vol. 86, abstract No. 156872x, p.66 (1977).

U. Rosentreter et al. Arzneim. Forsch/Drug Reasearch, vol. 39, No. 11, pp. 1519–1521 (1989).

*Primary Examiner*—Fiona T. Powers
*Attorney, Agent, or Firm*—Sprung Kramer Schaefer & Briscoe

[57] ABSTRACT

The invention relates to new [3-amino]-tetrahydrocarbazole-propanoic acid esters which can be used as intermediates for the preparation of known thromboxane-antagonistic active compounds, and to a method for the purification of these active compounds.

12 Claims, No Drawings

[3-AMINO]-TETRAHYDROCARBAZOLE-PROPANOIC ACID ESTERS

The invention relates to [3-Amino]-tetrahydrocarbazole-propanoic acid esters, processes for their preparation and their use for the synthesis of active compounds.

European Patent Application EP-242 518 discloses thromboxane-antagonistic active compounds of the following general formula,

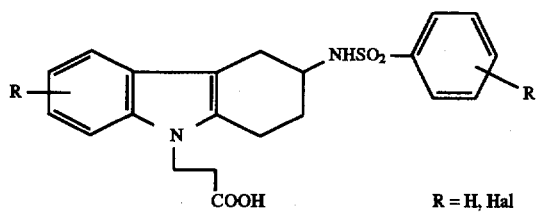

This application also describes the synthesis of these active compounds: Starting from the amine (A), which is first converted into the sulfonamide (B), addition of acrylonitrile is used to prepare the cyanoethyl-substituted compound (C), from which the active compound (D) is obtained by hydrolysis.

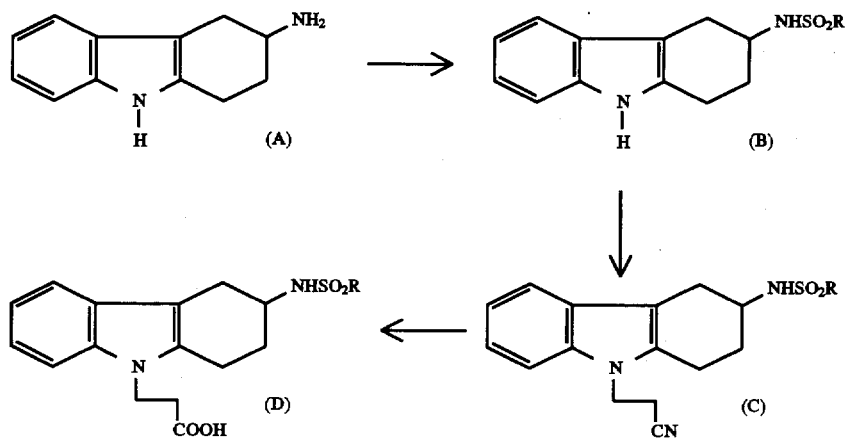

This preparation process, however, has crucial disadvantages: Completely apart from the fact that carcinogenic acrylonitrile is employed here [(B) to (C)], this process has other disadvantages. Thus, by means of the sulphonyl group, the N—H bond in the 3-position in (B) is acidified such that even this site is attacked by acrylonitrile, which leads to by-products. In addition, the drastic conditions needed for the hydrolysis of the nitrile to the carboxylic acid decrease the quality and yield of the final product.

There is therefore a great need for a possibility of preparing the known active compounds without the use of acrylonitrile, but in good yield and good quality (largely free of by-products).

The invention relates to [3-amino]-tetrahydrocarbazole-propanoic acid esters of the general formula (I)

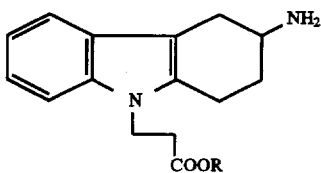

in which
R represents straight-chain or branched alkyl having up to 10 carbon atoms and their salts.

R preferably represents straight-chain or branched alkyl having 6 carbon atoms, particularly preferably having 4 carbon atoms.

The compounds according to the invention can also be present in the form of their salts. In the context of the invention, in general these are salts of the compounds according to the invention with inorganic or organic acids. Preferred salts are those with inorganic acids such as, for example, hydrochloric acid, hydrobromic acid, phosphoric acid or sulphuric acid or salts with organic carboxylic or sulphonic acids such as, for example, hydrochloric acid, hydrobromic acid, phosphoric acid or sulphuric acid or salts with organic carboxylic or sulphonic acids such as, for example, acetic acid, malonic acid, maleic acid, fumaric acid, malic acid, citric acid, tartaric acid, lactic acid, benzoic acid or methanesulphonic acid, ethanesulphonic acid, phenylsulphonic acid, toluenesulphonic acid, trifluoromethyl-sulphonic acid or naphthalenedisulphonic acid.

The compounds according to the invention can additionally exist in various stereoisomeric forms. Both the individual isomers (enantiomers/diastereomers) and their mixtures are a subject of the application.

Two processes for the preparation of the compounds of the general formula (I) have additionally been found, characterized in that Process A
tetrahydrocarbazoles of the general formula (II)

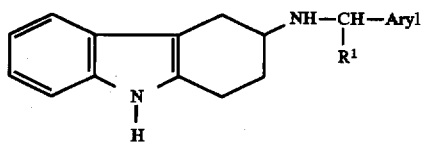

in which
$R^1$ represents hydrogen or methyl, and
Aryl represents optionally substituted naphthyl or phenyl, are reacted with acrylic esters of the formula (III)

$$H_2C=CH-COOR \quad (III)$$

if appropriate in inert solvents and if appropriate in the presence of auxiliaries, and then the group —CH(R$^1$)—aryl is removed, or Process B in that tetrahydrocarbazoles of the formula IV

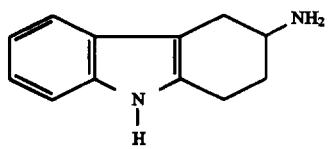

are reacted with acrylic esters (III), if appropriate in inert solvents and if appropriate in the presence of auxiliaries.

As compounds of the formula (IV) can also be prepared from the tetrahydrocarbazoles of the general formula (II) by removal of the benzyl groups, both processes can be illustrated by way of example by the following reaction scheme:

The processes according to the invention are in general carried out in a temperature range from −50° C. to +120° C., preferably from 0° to 80° C.

The processes according to the invention are in general carried out at normal pressure, but it is also possible to work at reduced pressure or elevated pressure.

The acrylic ester of the formula (III) is in general employed in an amount from 1 to 20 mol, preferably 1 to 10 mol, particularly preferably in an amount from 1 to 5 mol, calculated on the starting material (II).

The auxiliaries used are in general bases. Suitable bases in this context are the customary basic compounds such as alkali metal and alkaline earth metal hydroxides such as, for example, lithium, sodium or potassium hydroxide, or alkali metal alkoxides such as, for example, sodium methoxide or sodium ethoxide or potassium methoxide or potassium tert-butoxide. Preferred auxiliaries are sodium or potassium hydroxide.

Preferably, the process according to the invention is carried out in a two-phase system, consisting of water and a

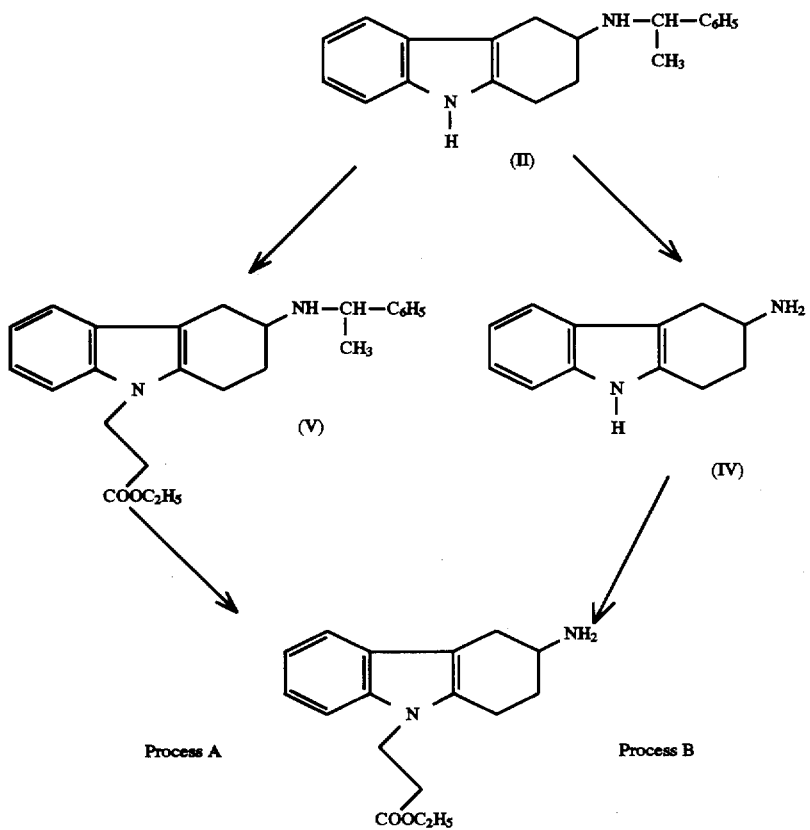

Reaction scheme

Solvents for the process according to the invention can be water and organic solvents which do not change under the reaction conditions. These preferably include polar aprotic solvents such as dimethylformamide, N-methylpyrrolidone, dimethyl sulphoxide or ethers such as diethyl ether, tetrahydrofuran, dioxane, glycol monomethyl or dimethyl ether, hydrocarbons such as benzene, toluene, xylene, cyclohexane, hexane or petroleum fractions, and chlorinated hydrocarbons such as, for example, dichloromethane, trichloromethane, tetrachloromethane or dichloroethylene. Ketones such as acetone, methyl ethyl ketone or methyl isobutyl ketone can additionally be used.

water-immiscible organic solvent in the presence of a suitable phase-transfer catalyst. Preferred solvent systems are mixtures of water with benzene, toluene, xylene, dichloromethane, tetrahydrofuran or methyl isobutyl ketone. A solid-liquid two-phase system is also preferred in which the auxiliaries are fed in anhydrous form into the solvents indicated.

Preferred phase-transfer catalysts are, for example, tetrabutyl-ammonium iodide, tetrabutyl-ammonium bromide, tetrabutyl-ammonium chloride, tributyl-methylphosphonium bromide, triethyl-C$_{13}$–C$_{15}$- alkylammonium chloride, trimethyl-$C_{13}$–$C_{15}$-alkylammonium bromide, dibenzyl-dimethyl-ammonium ethylsulphonate, dimethyl-$C_{12}$–$C_{15}$-alkylbenzylammonium chloride, dimethyl-$C_{12}$–$C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

Particularly preferred phase-transfer catalysts are benzyl-triethylammonium chloride and tetrabutylammonium bromide.

The removal of the group —CH(CH$_3$)C$_6$H$_5$ is carried out by customary methods by means of hydrogen with Pd catalysis under pressure or with salts of formic acid, e.g. ammonium formate with Pd catalysis and without pressure [cf., inter alia, Arzneim. Forsch./Drug Res. 3a 1519 [1989]].

The compounds according to the invention are suitable as intermediate compounds for the preparation of the active compounds disclosed in EP 242 518. The compounds of the general formula (I) can be hydrolysed in a simple manner to give the desired carboxylic acids after sulphonation on the 3-amino group. The advantage in this context is that the hydrolysis of the alkoxycarbonyl compound to the carboxyl compound takes place even at room temepmture using about 10% strength sodium hydroxide solution (2 hours at 50° C.) in contrast to the corresponding cyano compound, which needs 16 hours with potassium hydroxide solution at 100° C. for hydrolysis [cf. U. Rosentreter et. al, Arzneim. Forsch./Drug Res. 39, 1519 (1981)].

The compounds according to the invention can additionally be prepared in a simple manner as enantiomeric compounds, whereby the accessibility of enantiomerically pure final products is signficantly simplified.

The starting compound of the formula (II) has been disclosed (EP 242 518).

The acrylic esters of the formula (III) have likewise been disclosed.

EXAMPLE 1

Ethyl 3-[3R-(1-phenylethyl)-amino-1,2,3,4-tetrahydrocarbazol-9-yl]-propionate 0.127 mol of 3R-(1-phenylethyl)-amino-1,2,3,4-tetrahydrocarbazole (as the hydrochloride or sulphate) are suspended in about 125 ml of toluene, and the mixture is treated with 80 ml of about 10% strength sodium hydroxide solution and well stirred under reflux (about 84° C.) for about 30 minutes. 20 g of kieselguhr are added at 40° C. and the mixture is then filtered. The toluene phase of the filtrate is separated off and freed from water by distillation.

At about 50° C., 0.094 mol of anhydrous potash, 0.006 mol of benzyl-triethylammonium chloride and 0.156 mol of ethyl acrylate are added to the toluene solution. It is stirred at 80° C. for 90 minutes, treated with active carbon, cooled and filtered. The filtrate is concentrated on a rotary evaporator and the residue is recrystallized from isopropanol.

Yield: 81–85% of theory, content (HPLC)>98%; d.e.>98%.

EXAMPLE 2 tert-Butyl 3-[3R-(1-phenylethyl)-amino-1,2,3,4-tetrahydrocarbazol-9-yl]-propionate 0.2 mol of 3R-(1-phenylethyl)-amino-1,2,3,4-tetrahydrocarbazole hydrogensulphate and 0.2 mol of tetrabutylammonium bromide are dissolved in 250 ml of dichloromethane and treated with 130 ml of conc. sodium hydroxide solution. 0.22 mol of tert-butyl acrylate are added dropwise with good stirring at 10°–20° C. After stirring at about 20° C. for 6 hours, the mixture is diluted with water and the organic phase is separated off. The organic phase is evaporated in vacuo and the residue is recrystallized from isopropanol.

Yield 58% of theory; content (HPLC):>98% (m.p. 81° C.).

EXAMPLE 3 n-Butyl 3-[3R-(1-phenylethyl)-amino-1,2,3,4-tetrahydrocarbazol-9-yl]-propionate 0.1 mol of 3R-(1-phenylethyl)-amino-1,2,3,4-tetrahydrocarbazole (hydrochloride) is converted into the free base in toluene using sodium hydroxide solution (see Example 1). The toluene solution is evaporated and the residue is taken up in acetone. 0.1 mol of anhydrous potash, 0.005 mol of benzyltriethylammonium chloride and 0.12 mol of n-butyl acrylate are added to the acetone solution. It is stirred for 2.5 hours at reflux temperature, cooled and filtered, and the filtrate is evaporated to dryness. The residue is recrystallized from a little isopropanol. Yield 80% of theory, content (HPLC): 97%).

EXAMPLE 4 rac. Ethyl 3-[3-amino-1,2,3,4-tetrahydrocarbazol-9-yl]-propionate (hemisulphate)

A mixture of 0.4 mol of rac. 3-amino- 1,2,3,4-tetrahydrocarbazole, 0.3 mol of anhydrous potash, 0.08 mol of benzyltriethylammonium chloride and 0.6 mol of ethyl acrylate in about 500 ml of methyl isobutyl ketone is stirred at 90° C. for 45 minutes. Solid is then filtered off at about 60° C. The filtrate is evaporated in vacuo, the residue is dissolved in about 500 ml of ethanol and the solution is adjusted to pH>3 using about 20% sulphuric acid. The mixture is stirred for 1 h at 20° C., and the solid is filtered off and washed well with ethanol/water. The product is dried in vacuo.

Yield: 65–70% of theory; content as free base (HPLC) >78% (theoretical:)

Elemental analysis: product×0.5 H$_2$SO$_4$

The enantiomerically pure compound is obtained analogously to Example 4 (ee>98% of diastereomerically pure starting compound). (see Example 5).

EXAMPLE 5

Ethyl 3-[3R-amino-1,2,3,4-tetrahydrocarbazol-9-yl]-propionate (hemisulphate)

0.06 mol of ethyl 3-[3R-(1-phenylethyl)-amino-1,2,3,4-tetrahydrocarbazol-9-yl]-propionate (Example 1) are added to a suspension of 4.3 g of Pd on carbon (10% strength; 58.5% water-moist) in 35 ml of water and 80 ml of ethanol. 0.078 mol of ammonium formate is added and the mixture is stirred at reflux temperature for 1.25 hours. At about 75° C., 3–5 ml of acetic acid are added dropwise, the mixture is cooled to about 40° C. and insoluble material is filtered off. The filtrate is brought to pH>3 using about 20% strength sulphuric acid. The mixture is stirred at room temperature for about 1 hour, and the product is filtered off, washed with water/ethanol and dried.

Yield: 91% of theory; content as flee base (HPLC):>78% (ee>98).

EXAMPLE 6 tert-Butyl 3-[3R-amino-1,2,3,4-tetrahydrocarbazol-9-yl]-propionate 0.08 mol of tert-butyl 3-[3R-(1-phenethyl)-amino-1,2,3,4-tetrahydrocarbazol-1-yl]-propionate (Example 2), 24 g of Pd-C 5% strength (50% water) and 0.23 mol of ammonium formate are stirred for 20 minutes at about 70° C. in a mixture of 170 ml of ethanol and 70 ml of water. The catalyst is filtered off with suction and the solution is evaporated to dryness.

Yield: 91% of theory; m.p.: 83°–86° C.

EXAMPLE 7

Preparation and purification of (3R)-3-(4-fluorophenylsulphonamido)-1,2,3,4-tetrahydrocarbazol-9-yl-propionic acid (BAY u 3405):

0.414 mol of ethyl 3-[3R-amino-1,2,3,4-tetrahydrocarbazol-9-yl]-propionate hemisulphate (Example 5) is added to a solution of 0.515 mol of 4-fluorobenzenesulphonyl chloride in 450 ml of ethyl acetate. About 425 ml of 10% strength sodium hydroxide solution are added dropwise with cooling and stirring in the course of one hour (10°–15° C.). Stirring is continued for 30 minutes and the pH of the solution is adjusted from about 8 to about 5 using half-concentrated hydrochloric acid. The separated organic phase is largely evaporated on a rotary evaporator. The oily residue is treated with 350 ml of 10% strength sodium hydroxide solution and stirred at 50° C. for about 2 hours. It is cooled to 5° C. and covered with a layer of about 620 ml of ethyl acetate. A pH of 5 is established with continuous cooling using half-concentrated hydrochloric acid (about 180 ml).

The separated organic phase is evaporated on a rotary evaporator and taken up in about 650 ml of ethyl acetate. 66 ml of n-butylamine in 150 ml of ethyl acetate are added dropwise to the ethyl acetate solution. The mixture is stirred for 1 hour at 0° C., and the solid is filtered off with suction and washed 3 times with 60 ml of ethyl acetate each time. The isolated butylammonium salt (yield: quantitative: content>98%) can be recrystallized from isopropanol/ethyl acetate if required. The salt is dissolved in 440 ml of water, covered with a layer of 740 ml of ethyl acetate and slowly treated with cooling with about 220 ml of half-concentrated hydrochloric acid. The organic phase is washed twice with brine, dried over sodium sulphate and treated with 60 g of silica gel 60. The mixture is stirred for 30 minutes, the drying agent and silica gel are filtered off and the filter residue is washed twice with 70 ml of ethyl acetate each time. The filtrate collected is evaporated and the residue is crystallized from ethyl acetate/isohexane.

Yield: 85% of theory; content (HPLC): 98.9% [α]; 71° C. (c=1.0, MeOH)

We claim:

1. [3-Amino]-tetrahydrocarbazole-propanoic acid esters of the general formula (I)

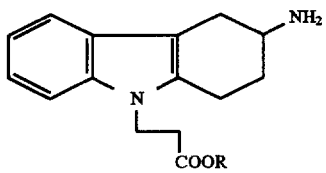

in which

R represents straight-chain or branched alkyl having up to 10 carbon atoms, and their salts.

2. A process for preparing a [3-amino]-tetrahydrocarbazole-propanoic acid ester according to claim 1, comprising reacting a tetrahydrocarbazole of the formula (IV):

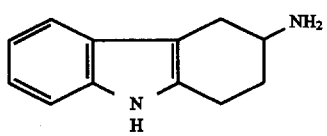

with an acrylic ester of the formula (III):

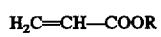

in which

R represents straight-chain or branched alkyl having up to 10 carbon atoms;

optionally in an inert solvent and optionally in the presence of an auxiliary.

3. Process according to claim 2, wherein the reaction is carried out in a temperature range from –50° C. to +120° C.

4. Process according to claim 2, wherein the reaction is carried out in a two-phase system, consisting of water and a water-insoluble organic solvent or in a two-phase system consisting of solid auxiliaries and an organic solvent.

5. Process according to claim 2, wherein the reaction is carried out with the aid of a phase-transfer catalyst.

6. A process for preparing a [3-amino]-tetrahydrocarbazole-propanoic acid ester according to claim 1, comprising (A) reacting a tetrahydrocarbazole of the formula (II):

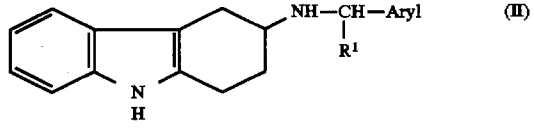

in which $R^1$ represents hydrogen or methyl; and

Aryl represents optionally substituted naphthyl or phenyl;

with an acrylic ester of the formula (III):

in which

R represents straight-chain or branched alkyl having up to 10 carbon atoms;

optionally in an inert solvent and optionally in the presence of an auxiliary; and (B) removing the group —CH($R^1$)—Aryl.

7. Process according to claim 6, wherein Aryl represents phenyl and the group —CH($R^1$)$C_6H_5$ is first removed from the tetrahydrocarbazole of the formula (II), which is then reacted with acrylates of the formula (III).

8. Process according to claim 6, wherein the reaction is carried out in a temperature range from –50° C. to +120° C.

9. Process according to claim 6, wherein reaction step (A) is carried out in a two-phase system, consisting of water and a water-insoluble organic solvent or in a two-phase system consisting of solid auxiliaries and an organic solvent.

10. Process according to claim 6, wherein characterized in that reaction Step (A) is carried out with the aid of a phase-transfer catalyst.

11. A process for preparing a [3-arylsulphonylamino]-tetrahydrocarbazole-propionic acid compound of the formula:

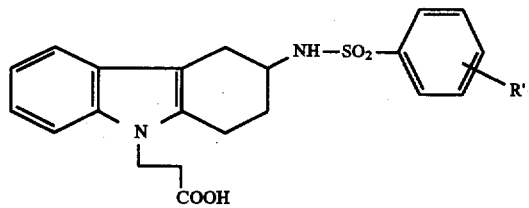

comprising:

(A) preparing a [3-amino]-tetrahydrocarbazole-propionic acid ester of the formula (I):

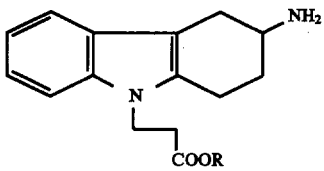

in which

R represents straight-chain or branched alkyl having up to 10 carbon atoms;

according to the process of claim 2;

(B) reacting the [3-amino]-tetrahydrocarbazole-propionic acid ester of the formula (I) with a phenylsulphonyl chloride of the formula:

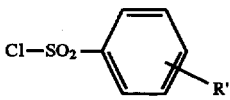

wherein

R' represents hydrogen or halogen;

to form a product of the formula:

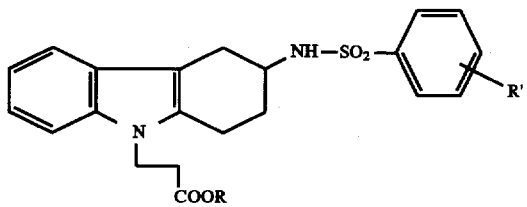

and (c) hydrolyzing the product of (B).

12. A process for preparing a [3-arylsulphonylamino]-tetrahydrocarbazole-propionic acid compound of the formula:

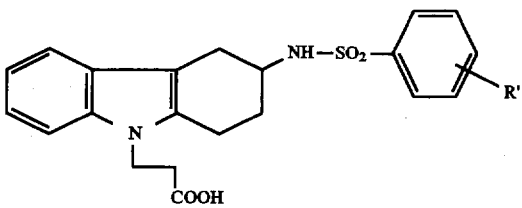

comprising:

(A) preparing a [3-amino]-tetrahydrocarbazole-propionic acid ester of the formula (I):

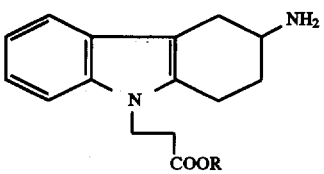

in which

R represents straight-chain or branched alkyl having up to 10 carbon atoms; according to the process of claim 6;

(B) reacting the [3-amino]-tetrahydrocarbazole-propionic acid ester of the formula (I) with a phenylsulphonyl chloride of the formula:

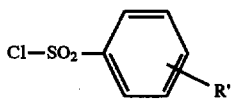

wherein

R' represents hydrogen or halogen;

to form a product of the formula:

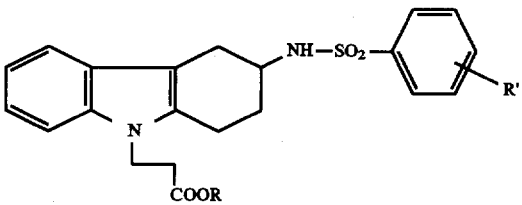

and (c) hydrolyzing the product of (B).

* * * * *

UNITED STATES PATENT AND TRADEMARK OFFICE
CERTIFICATE OF CORRECTION

PATENT NO. : 5,684,158
DATED : November 4, 1997
INVENTOR(S) : Samaan, et al.

It is certified that error appears in the above-indentified patent and that said Letters Patent is hereby corrected as shown below:

Col. 9, lines 5-6  Delete " characterized in that "

Signed and Sealed this

Twenty-fourth Day of November, 1998

Attest:

Attesting Officer

BRUCE LEHMAN

Commissioner of Patents and Trademarks